US00PP13706P39

(12) United States Plant Patent
Hirsch et al.

(10) Patent No.: US PP13,706 P3
(45) Date of Patent: Apr. 1, 2003

(54) BRUNNERA PLANT NAMED 'SILVER WINGS'

(76) Inventors: Jack E. Hirsch, 2610 W. Valley Rd., Chimacum, WA (US) 98325; Gary T. Lindheimer, 2610 W. Valley Rd., Chimacum, WA (US) 98325

( * ) Notice: Subject to any disclaimer, the term of this patent is extended or adjusted under 35 U.S.C. 154(b) by 13 days.

(21) Appl. No.: 09/907,878

(22) Filed: Jul. 17, 2001

(65) Prior Publication Data

US 2003/0019003 P1 Jan. 23, 2003

(51) Int. Cl.[7] ..... A01H 5/00
(52) U.S. Cl. ..... Plt./263
(58) Field of Search ..... Plt./263

(56) References Cited

PUBLICATIONS

Http://www.glossary.gardenweb.com.*
http://www.tiscali.co.uk/reference/dictionaries/difficult-words/data/d0001471.html.*

* cited by examiner

*Primary Examiner*—Bruce R. Campell
*Assistant Examiner*—W C Haas
(74) *Attorney, Agent, or Firm*—Mark P. Bourgeois

(57) ABSTRACT

A new cultivar of Brunnera named 'Silver Wings' that is characterized by gray-green foliage that is variegated with thin cram-white margins and a silver overlay on the surface of the leaves. 'Silver Wings' exhibits a clumping habit and small clusters of violet-blue flowers are present in late spring. In combination these traits set 'Silver Wings' apart from all other existing varieties of Brunnera known to the inventor.

4 Drawing Sheets

Botanical classification: *Brunnera Macrophylla.*
Variety denomination: 'Silver Wings'.

BACKGROUND OF THE INVENTION

The present invention relates to a new and distinct cultivar of Siberian Bugloss that is a fast growing perennial with a clumping habit, grown for use in borders or as an accent plant. The new cultivar is known botanically as a *Brunnera macrophylla* and will be referred to hereinafter by the cultivar name 'Silver Wings'.

'Silver Wings' was discovered by the inventors in 1997 in a cultivated area of Chimacum, Wash. as a sport in a flat of tissue cultured *Brunnera macrophylla* 'Langtrees' (unpatented). The distinguishing characteristics of 'Silver Wings' are the thin cream-white margin on the leaves, the silver overlay on the surface of the leaves, and the leaves resistance to burning. The closest comparison plants are *Brunnera macrophylla* 'Variegata' (unpatented) and the parent *Brunnera macrophylla* 'Langtrees'. 'Silver Wings' is distinguishable from 'Langtrees' by the silver overlay on the surface of the leaves. 'Silver Wings' is unique from 'Variegata' because unlike 'Variegata', its leaves are resistant to burning. When planted in partial shade and moist soil 'Silver Wings' maintains a clean and vigorous appearance all season.

'Silver Wings' was first asexually propagated by the inventors in 1998 in Chimacum, Wash. by division. Since that time, under careful observation, the distinguishing characteristics have been determined stable and uniform in successive generations.

SUMMARY OF THE INVENTION

The following represent the distinguishing characteristics of the new Brunnera cultivar 'Silver Wings'. In combination these traits set 'Silver Wings' apart from all other existing varieties of Brunnera known to the inventor. 'Silver Wings' has not been tested under all possible conditions and phenotypic differences may be observed with variations in environmental, climatic, and cultural conditions, however, without any variance in genotype.

1. Brunnera 'Silver Wings' exhibits variegated foliage that is gray-green with a silver overlay on the surface of the leaves and thin cream-white margins.

2. Brunnera 'Silver Wings' is a small to medium size perennial grown for use in borders or as an accent plant.

3. Brunnera 'Silver Wings' is a prolific bloomer producing clusters of tiny violet-blue flowers in mid to late spring.

4. Brunnera 'Silver Wings' grows to 60 cm. in height and 60 cm. in width at maturity.

5. The foliage of Brunnera 'Silver Wings' is resistant to burning.

6. Brunnera 'Silver Wings' exhibits a clumping habit.

BRIEF DESCRIPTION OF THE DRAWINGS

The accompanying color photographs illustrate the distinguishing traits of the new cultivar. The plant on sheet 1,2 &3 is twelve months and was grown in a greenhouse in Arroyo Grande, Calif. in a two-gallon container. The plants on sheet 4 are six months and were grown in a greenhouse in four-inch containers.

The photograph on sheet 1 illustrates the plant from a side perspective.

The photograph on sheet 2 is a close-up view of the foliage.

The photograph on sheet 3 is a close-up view of the flower.

The photograph on sheet 4 compares 'Silver Wings' on the lower left to 'Langtrees' (prior art) on the lower right and 'Variegata' above center. All photographs are taken using conventional techniques and although foliage colors may appear different from actual colors due to light reflectance, they are as accurate as possible by conventional photography.

BOTANICAL DESCRIPTION OF THE PLANT

The following is a detailed description of the Brunnera cultivar named 'Silver Wings'. Data was collected in Arroyo Grande, Calif. from the inventor and from plants that are 12 months and grown in a greenhouse in two-gallon containers. Color determinations are in accordance with The Royal Horticultural Society Colour Chart except where general color terms of ordinary dictionary significance are used. The growing requirements are similar to the species.

Botanical classification: *Brunnera macrophylla* 'Silver Wings'.
Common name: Siberian Bugloss.
Use: Accent and perennial border plant.
Parentage: 'Silver Wings' is a sport of *Brunnera macrophylla* 'Langtrees'.
Vigor: Highly vigorous.
Habit: Clumping.
Height: 60 cm. in height.
Width: 60 cm. in width.
Hardiness: USDA Zone 4.
Propagation: Division, root cuttings and meristem tissue culture using a dormant eye.
Root system: Rhizomatous.
Cultural requirements: Plant in partial shade and moist but well-drained soils.
Type: Perennial herb.
Time to initiate roots: Approximately four weeks are required to produce roots on an initial cutting.
Crop time: Approximately 6–9 months are required to produce a finished one-gallon from a rooted cutting.
Seasonal interest: Flowers in spring and variegated foliage year round.
Stem:
- *Branching habit.*—Basal branching rosette.
- *Stem diameter.*—3 mm. in diameter.
- *Stem length.*—16 cm. in length.
- *Shape.*—Mostly cylindrical but with a depressed furrow on one side creating a C-shape in cross section.
- *Surface.*—Setose.
- *Branch color.*—148B.

Foliage:
- *Leaf arrangement.*—The primary leaves are one solitary leaf on each basal stem. The secondary leaves are alternate on the peduncle.
- *Leaf division.*—Simple.
- *Leaf margin.*—Entire.
- *Leaf shape.*—Deltoid.
- *Leaf base.*—The primary leaves on the stems exhibit an auriculate base and the smaller secondary leaves on the peduncle exhibit a truncate base.
- *Leaf attachment on peduncle.*—Sessile.
- *Leaf apex.*—Acute.
- *Leaf venation.*—Pinnate with veins depressed on adaxial surface and protruding on abaxial surface.
- *Vein color* (*adaxial surface*).—138A.
- *Vein color* (*abaxial surface*).—138A.
- *Leaf surface* (*adaxial*).—Setose.
- *Leaf surface* (*abaxial*).—Setose.
- *Leaf texture.*—Slightly rough.
- *Stipules.*—Absent.
- *Leaf length* (*primary leaf*).—10 cm. in length.
- *Leaf width* (*primary leaf*).—9.5 cm. in width.
- *Leaf length* (*secondary leaf on peduncle*).—3 cm. in length.
- *Leaf width* (*secondary leaf on peduncle*).—2.75 cm. in width.
- *Leaf color* (*adaxial surface*).—Mostly 138A with a silver overlay of 202D and margins that are 158B.
- *Leaf color* (*abaxial surface*).—Mostly 138B with a silver overlay of 202D and a margin that is 158B.
- *Foliar fragrance.*—Absent.

Flower:
- *Flower sexuality.*—Bisexual.
- *Form.*—Terminal panicle.
- *Dimensions of panicle.*—17 cm. in length and 7 cm. in width.
- *Quantity of flowers per panicle.*—8–10 flowers.
- *Shape of flower.*—Rotate.
- *Flower markings.*—A pale violet-blue raised ring at the center of the flower and darker violet-blue markings at the rings perimeter.
- *Color of ring.*—97D.
- *Color of darker perimeter.*—97A.
- *Symmetry.*—Symmetrical.
- *Aspect.*—Facing upward.
- *Color of flower petal.*—Overall color is 97C with markings that are 97A and 97D.
- *Number of petals.*—Five.
- *Petal shape.*—Obicular.
- *Petal surface.*—Smooth.
- *Petal length.*—3 mm in length.
- *Petal width.*—3 mm in width.
- *Unfused or fused.*—Petals are basally fused.
- *Bud color.*—97B.
- *Bud shape.*—Globose.
- *Bud dimensions.*—1.5 mm. in length and 1.5 mm. in diameter.
- *Dimensions of open flower.*—3 mm. in diameter and 3 mm. in length.
- *Persistent or self-cleaning.*—Self-cleaning.
- *Shape of calyx.*—Campanulate.
- *Color of calyx.*—144A.
- *Dimensions of calyx.*—1.5 mm. in diameter and 1.75 mm. in length.
- *Number of sepals.*—Five sepals.
- *Fused or unfused.*—Basally fused.
- *Sepal color.*—144A.
- *Dimensions of sepal.*—0.50 mm. in width and 1.75 mm. in length.
- *Blooming period.*—April to May.
- *Peduncle* (*primary*).—17 to 23 cm. in length and 3 mm. in diameter.
- *Peduncle* (*secondary*).—4 cm. in length and less than 1 mm. in width.
- *Color of peduncle.*—144B.
- *Surface of peduncle.*—Setose and fluted.
- *Fragrance.*—Absent.

Reproduction organs:
- *Stamens.*—Five stamens that are included and inserted in the middle of the corolla tube.
- *Color of stamens.*—200D.
- *Dimensions of stamen.*—Less than 1 mm. in height and less than 1 mm. in width.
- *Dimensions of anther.*—Less than 0.50 mm. in height and less than 0.50 mm. in width.
- *Pollen color.*—158D.
- *Style.*—Included.

*Style color.*—155B.

*Style dimensions.*—Less than 0.25 mm. in length and less than 0.25 mm in width.

*Stigma.*—Capitate.

*Stigma color.*—155B.

*Stigma dimensions.*—Less than 0.25 mm. in length and less than 0.25 mm in width.

*Ovary position.*—Superior.

*Ovary color.*—155B.

*Ovary dimensions.*—Less than 0.50 mm. in diameter and less than 0.50 mm. in height.

Seed: Seed production has not been observed.

We claim:

1. A new and distinct variety of Brunnera plant named 'Silver Wings' as described and illustrated.

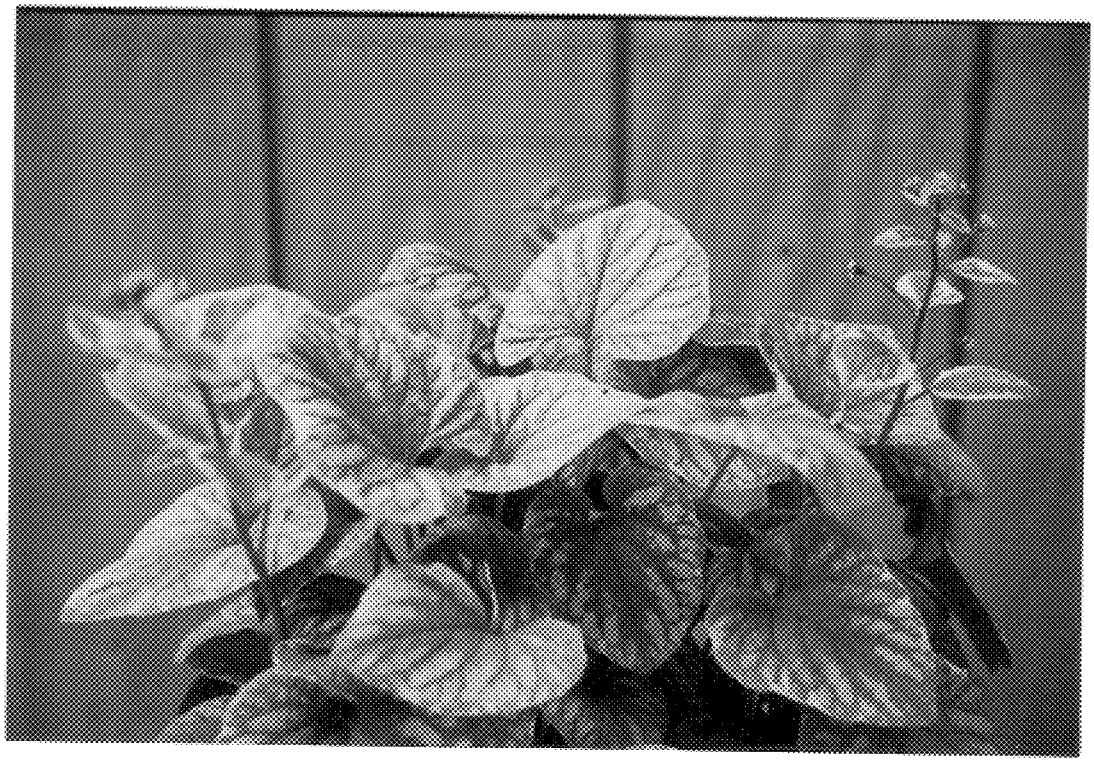

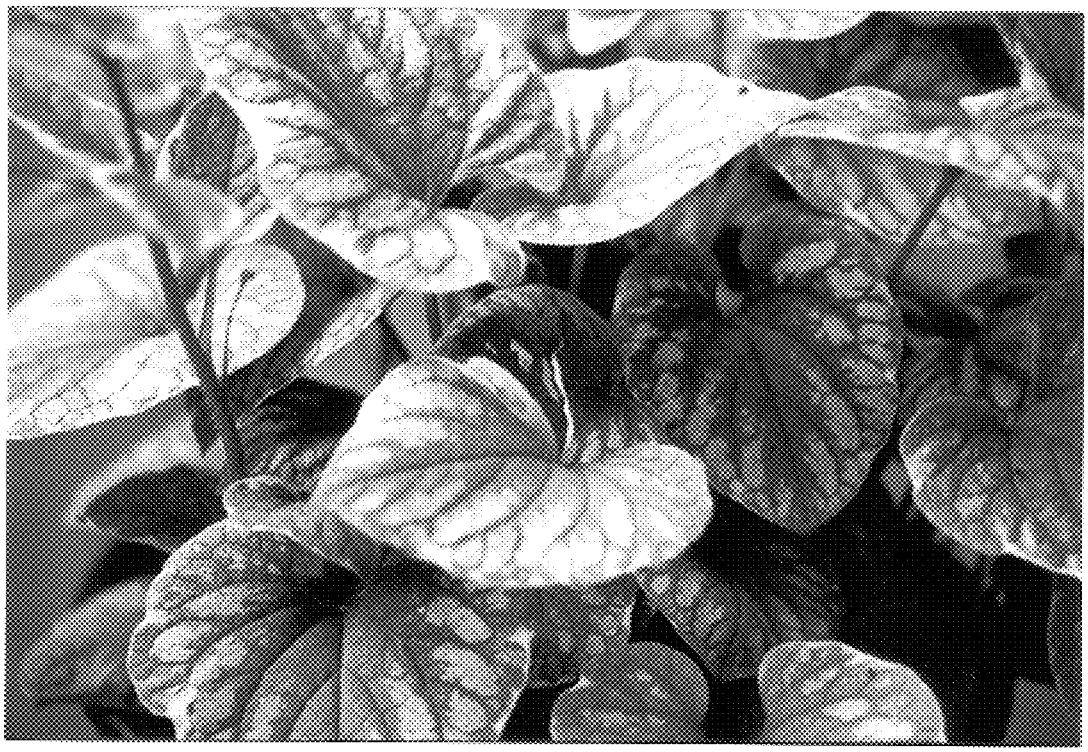

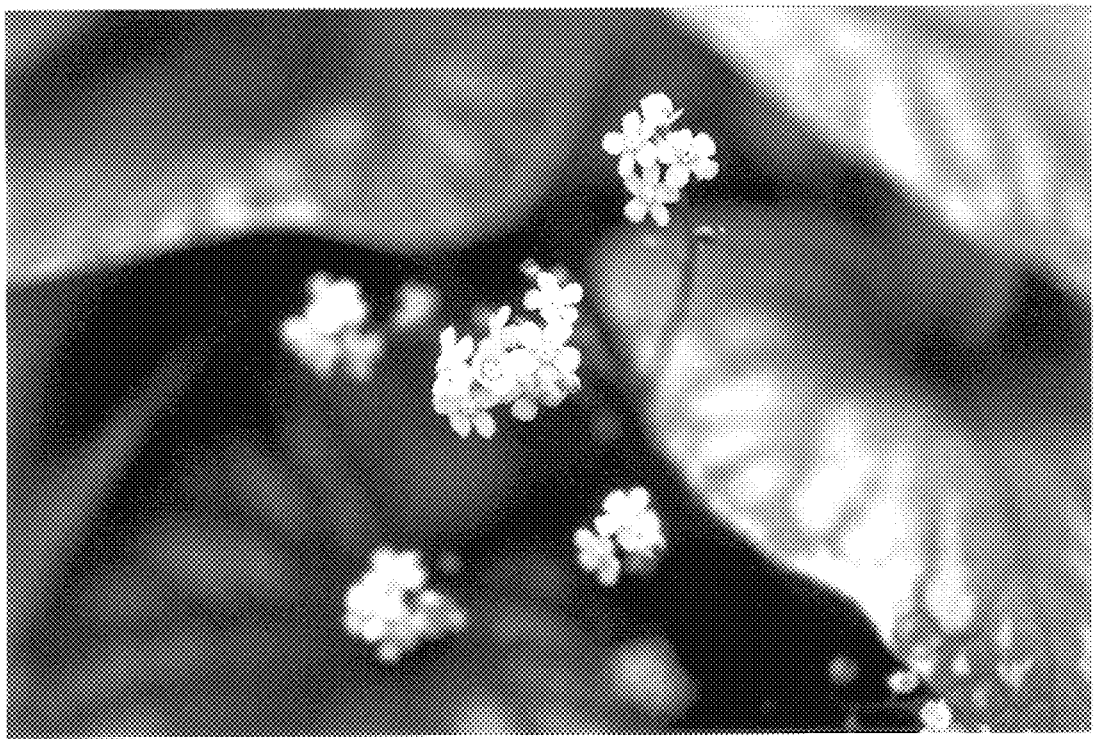

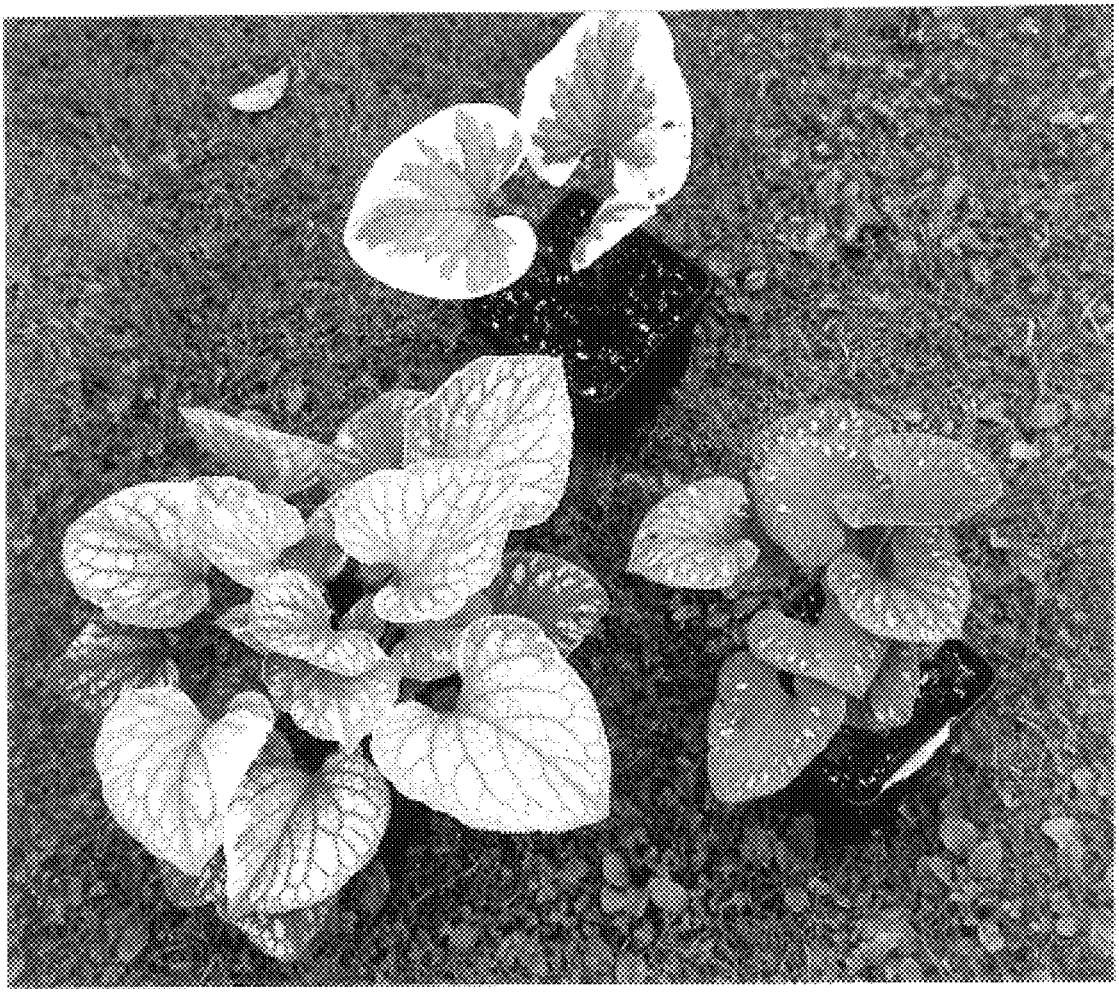

* * * * *